US012059501B2

(12) United States Patent
Hiramura et al.

(10) Patent No.: US 12,059,501 B2
(45) Date of Patent: Aug. 13, 2024

(54) METHOD FOR PRODUCING DISINTEGRATING PARTICULATE COMPOSITION COMPRISING ACID-TYPE CARBOXYMETHYLCELLULOSE, DISINTEGRATING PARTICULATE COMPOSITION COMPRISING ACID-TYPE CARBOXYMETHYLCELLULOSE, AND ORALLY DISINTEGRATING TABLET INCLUDING DISINTEGRATING PARTICULATE COMPOSITION COMPRISING ACID-TYPE CARBOXYMETHYLCELLULOSE

(71) Applicants: DAICEL CORPORATION, Osaka (JP); NICHIRIN CHEMICAL INDUSTRIES, LTD., Hyogo (JP)

(72) Inventors: Takahiro Hiramura, Tokyo (JP); Kiyoshi Ikura, Tokyo (JP); Sae Itaya, Tokyo (JP); Tomohito Okabayashi, Tokyo (JP); Naohiro Hashikawa, Tokyo (JP); Tetsuro Morita, Hyogo (JP); Kimiko Ikeda, Hyogo (JP); Haruka Wakayama, Hyogo (JP)

(73) Assignees: DAICEL CORPORATION, Osaka (JP); NICHIRIN CHEMICAL INDUSTRIES, LTD., Hyogo (JP)

( * ) Notice: Subject to any disclaimer, the term of this patent is extended or adjusted under 35 U.S.C. 154(b) by 0 days.

(21) Appl. No.: 16/600,066

(22) Filed: Oct. 11, 2019

(65) Prior Publication Data
US 2020/0038332 A1 Feb. 6, 2020

Related U.S. Application Data

(62) Division of application No. 14/384,358, filed as application No. PCT/JP2013/059083 on Mar. 27, 2013, now abandoned.

(30) Foreign Application Priority Data

Mar. 29, 2012 (JP) .................. 2012-075832
Sep. 20, 2012 (JP) .................. 2012-206895
Sep. 20, 2012 (JP) .................. 2012-206896
Dec. 18, 2012 (JP) .................. 2012-275942

(51) Int. Cl.
*A61K 9/20* (2006.01)
*A61K 9/00* (2006.01)

(52) U.S. Cl.
CPC .......... *A61K 9/2054* (2013.01); *A61K 9/0056* (2013.01); *A61K 9/2018* (2013.01); *A61K 9/2027* (2013.01); *A61K 9/2095* (2013.01)

(58) Field of Classification Search
CPC .. A61K 9/0056; A61K 9/2018; A61K 9/2027; A61K 9/2054; A61K 9/2095; A61K 47/36; A61K 47/38

USPC ......................................... 514/772
See application file for complete search history.

(56) References Cited

U.S. PATENT DOCUMENTS

| | | | |
|---|---|---|---|
| 2,851,453 A | 9/1958 | Kennon et al. | |
| 7,510,728 B2* | 3/2009 | Koike | A61P 3/10 |
| | | | 424/475 |
| 9,446,055 B2* | 9/2016 | Fujiwara | A61K 31/616 |
| 9,974,738 B2* | 5/2018 | Hiramura | A61K 9/1652 |
| 10,130,584 B2* | 11/2018 | Hiramura | A61K 9/1623 |
| 10,959,916 B2* | 3/2021 | Hamasaki | A61K 47/42 |
| 2006/0127475 A1 | 6/2006 | Makino et al. | |
| 2011/0053942 A1 | 3/2011 | Fujiwara et al. | |
| 2011/0150989 A1* | 6/2011 | Park | A61K 9/209 |
| | | | 424/457 |
| 2011/0287099 A1* | 11/2011 | Liang | A61P 3/06 |
| | | | 424/468 |

(Continued)

FOREIGN PATENT DOCUMENTS

| | | |
|---|---|---|
| EP | 1 329 217 | 7/2003 |
| EP | 1 980 272 | 10/2008 |
| EP | 2 251 005 | 11/2010 |

(Continued)

OTHER PUBLICATIONS

Lieberman et al., Pharmaceutical dosage forms: tablets vol. 1, 1989, Marcel Dekker INC, second edition, pp. 1-593 (Year: 1989).*

(Continued)

Primary Examiner — Isaac Shomer
Assistant Examiner — Amanda Michelle Petritsch
(74) Attorney, Agent, or Firm — Morgan, Lewis & Bockius LLP

(57) ABSTRACT

The present application provides an orally-disintegrating tablet having excellent tablet hardness and disintegrability. The present application further provides a method of producing a disintegrative particulate composition including three components consisting of a first disintegrator component of an acid-type carboxymethylcellulose, a second disintegrator component and an excipient. The method includes a first wet granulation step using any two of the three components, and a second wet granulation step using granules obtained in the first wet granulation step and the remaining one component of the three components not used in the first wet granulation step. The production method may further includes a crystalline cellulose as a fourth component or a third step of mixing a crystalline cellulose into granules obtained in the second wet granulation step. Disintegrative particulate compositions obtained by these methods are also disclosed.

20 Claims, No Drawings

(56) References Cited

U.S. PATENT DOCUMENTS

2012/0156261 A1* 6/2012 Fujiwara .............. A61K 9/2018
514/630
2013/0273153 A1* 10/2013 Park .................... A61K 31/485
424/452

FOREIGN PATENT DOCUMENTS

| EP | 2 368 544 | 9/2011 |
| EP | 2 465 495 | 6/2012 |
| EP | 2 465 539 | 6/2012 |
| EP | 2 832 350 | 2/2015 |
| EP | 2 898 899 | 7/2015 |
| JP | 10-182436 | 7/1998 |
| JP | 2000-273039 | 10/2000 |
| JP | 2002-179558 | 6/2002 |
| JP | 2007-153887 | 6/2007 |
| JP | 2008-285434 | 11/2008 |
| JP | 4551627 | 9/2009 |
| JP | 2010-529074 | 8/2010 |
| JP | 2012-31138 | 2/2012 |
| JP | 2012046446 A * | 3/2012 |
| JP | 2013-147470 | 8/2013 |
| TW | 1 376 243 | 11/2012 |
| WO | 2011/019043 | 2/2011 |
| WO | 2011/019045 | 2/2011 |
| WO | 2012/087377 | 6/2012 |
| WO | 2013/146917 | 10/2013 |

OTHER PUBLICATIONS

JP-2012046446-A Google patents translation (Year: 2012).*
Reier, G. E. et al., "Microcrystalline Cellulose in Tableting", Journal of Pharmaceutical Sciences, 1966, vol. 55(5), pp. 510-514.
Gissinger, D. et al., "A Comparative Evaluation of the Properties of some Tablet Disintegrants", Drug Development and Industrial Pharmacy, 1980, vol. 6(5), pp. 511-536.
International Search Report (ISR) (PCT Form PCT/ISA/210) in International Patent Application No. PCT/JP2013/059083 mailed on Jun. 25, 2013.
Supplementary European Search Report of Application No. EP13 76 7870 mailed Oct. 19, 2015.
Extended European Search Report issued in European Patent Application No. 13 84 0080, issued Feb. 11, 2016.
International Search Report, issued in International Patent Application No. PCT/JP2014/075241, mailed Dec. 22, 2014.
File History of U.S. Appl. No. 14/384,358, filed Oct. 11, 2014.

* cited by examiner

METHOD FOR PRODUCING DISINTEGRATING PARTICULATE COMPOSITION COMPRISING ACID-TYPE CARBOXYMETHYLCELLULOSE, DISINTEGRATING PARTICULATE COMPOSITION COMPRISING ACID-TYPE CARBOXYMETHYLCELLULOSE, AND ORALLY DISINTEGRATING TABLET INCLUDING DISINTEGRATING PARTICULATE COMPOSITION COMPRISING ACID-TYPE CARBOXYMETHYLCELLULOSE

This application is a Divisional of U.S. application Ser. No. 14/384,358, filed on Oct. 11, 2014, which is a national stage application of International Patent Application No PCT/JP2013/059083, filed Mar. 27, 2013, which claims priority to Japanese Patent Application No. 2012-075832, filed Mar. 29, 2012; Japanese Patent Application No. 2012-206895, filed Sep. 20, 2012; Japanese Patent Application No. 2012-206896, filed Sep. 20, 2012 and Japanese Patent Application No. 2012-275942, filed Dec. 18, 2012. The entirety of the aforementioned applications is incorporated herein by reference.

FIELD

The present invention relates to a disintegrative particulate composition which includes an acid-type carboxymethylcellulose and which can be produced by a multi-stage granulation process, and a method of producing the same, as well as an orally-disintegrating tablet including the composition.

BACKGROUND

In the past, orally-disintegrating tablets have been developed as highly convenient forms which can safely be taken by patients who have difficulty in swallowing drugs, elderly people, children, etc. and which can easily be taken without water. It is important that orally-disintegrating tablets have sufficient breaking strength (tablet hardness) such that any cracks, powdering, etc. are not caused in the tablets during production or transportation of the tablets or during breaking the seals in the same manner as general tablets, and also, it is important that orally-disintegrating tablets have excellent disintegrability (disintegration time) such that the tablets immediately disintegrate in the oral cavity.

Moreover, superior moldability has been sought in production of tablets. The term "moldability" here refers to a relation between the tablet compression force and the tablet hardness resulting therefrom. In production methods which require high tablet compression forces, there may be problems such as limitations in performance of tablet machines, a decrease in the productivity, and deterioration in functions of coating fine particles included in tablets. Therefore, it is also important that particles or particulate compositions constituting tablets have superior moldability, i.e. properties that can provide a higher tablet hardness by using the same tablet compression force or that can achieve the same tablet hardness by a lower tablet compression force.

Tablet hardness and disintegrability are mutually opposing properties. In general, when the molding pressure is increased to increase the hardness, the disintegration time tends to be prolonged, and, when the molding pressure is reduced to shorten the disintegration time, the hardness tends to be smaller. Therefore, various technologies have been developed in order to combine the two properties or to achieve an optimal balance between the two properties.

Furthermore, components of the particles, granulation methods, etc. have been studied in order to impart superior moldability to particles or particulate compositions constituting tablets.

Additionally, an acid-type carboxymethylcellulose is a cellulose derivative otherwise called "carmellose", and this substance has properties that, when water is added to the substance, the substance swells but converts into a suspension having almost no viscosity. Therefore, an acid-type carboxymethylcellulose has been used as an ingredient for orally-disintegrating tablets, namely as a base, binder, excipient or disintegrator therefor.

Also, a crystalline cellulose is a white water-insoluble powdery substance obtained by partially depolymerizing α-cellulose, which is obtained from fibrous plants, with acids, followed by purification. A crystalline cellulose has no taste, and, since the substance is chemically inactive, it does not change even when being mixed with medicaments. Therefore, a crystalline cellulose has been used for purposes of a pharmaceutical additive, in particular, an excipient, binder, disintegrator or the like for preparing tablets. In addition, a crystalline cellulose has been used as an emulsification stabilizer or the like for cosmetics, dairy products, etc. besides an additive for pharmaceuticals.

For example, PTL 1 describes a disintegrative particulate composition which is produced through homogeneous dispersion of mannitol, xylitol, an inorganic excipient, a disintegrator and carmellose in the presence of water, followed by drying the dispersion. The composition is characterized in that composite particles including xylitol dispersed in mannitol particles in the solid state are formed, and that the inorganic excipient, the disintegrator and carmellose are dispersed in the composite particles. The disintegrative particulate composition is produced through spray granulation of a dispersion obtained by dispersing these components in an aqueous medium, or is produced by spraying the dispersion to carriers such as of mannitol.

Also, PTL 2 describes an orally-disintegrating tablet which contains an active ingredient and 10% (w/w) or more of carboxymethylcellulose relative to the total amount. The components are mixed, and then, the orally-disintegrating tablet is prepared with a tablet machine.

Moreover, PTL 3 describes a method of producing an orally-disintegrating tablet which contains loratadine as a medicinal ingredient. This production method is characterized in that two-stage granulation steps are carried out therein, i.e. loratadine and at least one type of an additive such as a binder, excipient, or disintegrator are granulated in the first granulation step, and, in the second granulation step, granules obtained in the first granulation step are further granulated together with at least one type of the same additive such as a binder, excipient, or disintegrator as that used in the first granulation step. As one example of the disintegrator, carmellose is mentioned therein.

Furthermore, PTL 4 describes a method of producing an orally-disintegrating tablet. The production method includes a step of spraying a water suspension of a water-soluble but hydrophilic disintegrating component onto a mixture of an excipient and a medicament to obtain granules A including the medicament; a step of spraying the same water suspension of the disintegrating component onto the excipient to obtain granules B not including the medicament; and a step of subjecting the resulting granules A and B to compression molding.

CITATION LIST

Patent Literature

PTL 1: International Publication Pamphlet No. WO 2011/019045
PTL 2: JP-A-2008-285434
PTL 3: JP-A-2012-31138
PTL 4: Specification of Japanese Patent No. 4551627

DETAILED DESCRIPTION

Technical Problem

The problem to be solved by the present invention is to provide a disintegrative particulate composition, including an acid-type carboxymethylcellulose as a disintegrator component, which can impart excellent tablet hardness and disintegrability to an orally-disintegrating tablet to which the composition is added, and which further imparts, to the orally-disintegrating tablet, excellent moldability where sufficient tablet hardness can be obtained through the moldability even by a practical and comparatively-low tablet compression force in production of the tablet, and to further provide a method of producing the same, etc.

In addition, a problem was observed in conventional technologies, in which, when producing a disintegrative particulate composition and an orally-disintegrating tablet including the composition, addition of a crystalline cellulose as an excipient increased the tablet hardness but reduced the disintegrability (prolonged the disintegration time).

Accordingly, another object of the present invention is to solve such a problem, and thus, is to provide a method of producing a disintegrative particulate composition which can enhance the tablet hardness while maintaining sufficient disintegrability (maintaining the short disintegration time) even upon addition of a crystalline cellulose, and to provide a disintegrative particulate composition obtained by the production method, as well as an orally-disintegrating tablet including the composition, etc.

Solution to Problem

The present inventors carried out intensive studies in order to solve the above-described problems. Consequently, the present inventors found that, in producing a disintegrative particulate composition including three components which are a first disintegrator component of an acid-type carboxymethylcellulose, a second disintegrator component other than the acid-type carboxymethylcellulose and an excipient, a disintegrative particulate composition providing superior tablet hardness and disintegrability, or higher tablet hardness without substantially prolonging the disintegration time could be produced by a method mentioned below, as compared with a method in which the three components were used and granulated together in one step, although both the disintegrative particulate compositions included the same components. That is, said method includes a first wet granulation step using any two components of the three components, and a second wet granulation step using at least granules obtained in the first wet granulation step and the remaining one component not used in the first wet granulation step. And also, the present inventors found that the composition exhibited higher moldability in production of tablets.

Furthermore, the present inventors found that a disintegrative particulate composition having higher tablet hardness while maintaining sufficient disintegrability could be produced by adding a crystalline cellulose as a forth component to the disintegrative particulate composition produced in the above-mentioned way, and found that excellent tablet hardness and disintegrability were imparted to an orally-disintegrating tablet which was produced by mixing said disintegrative particulate composition with a drug. The present invention was completed based on these findings.

More specifically, the present invention is to provide the following embodiments.

Embodiment 1

An method of producing a disintegrative particulate composition including three components consisting of a first disintegrator component of an acid-type carboxymethylcellulose, a second disintegrator component other than the acid-type carboxymethylcellulose and an excipient, wherein the method includes a first wet granulation step using any two of the three components; and a second wet granulation step using at least granules obtained in the first wet granulation step and the remaining one component not used in the first wet granulation step.

Embodiment 2

The method of producing a disintegrative particulate composition according to Embodiment 1, wherein the disintegrative particulate composition further includes a crystalline cellulose as a forth component, and the method includes a first wet granulation step using any two or three of the four components and a second wet granulation step using at least the granules obtained in the first wet granulation step and the remaining one or two of the four components not used in the first wet granulation step.

Embodiment 3

The method of producing a disintegrative particulate composition according to Embodiment 1, wherein the disintegrative particulate composition further includes a crystalline cellulose as a forth component, and the method includes a first wet granulation step using any two of the three components other than the crystalline cellulose, a second wet granulation step using at least the granules obtained in the first wet granulation step and the remaining one component not used in the first wet granulation step, and a third step of mixing the crystalline cellulose into granules obtained in the second wet granulation step.

Embodiment 4

The method of producing a disintegrative particulate composition according to any one of Embodiments 1 to 3, wherein any of the four components is used only in one granulation step.

Embodiment 5

The method of producing a disintegrative particulate composition according to Embodiment 4, wherein the method includes the first wet granulation step using any two of the three components and the second wet granulation step using only the granules obtained in the first wet granulation step and the remaining one component not used in the first wet granulation step.

Embodiment 6

The method of producing a disintegrative particulate composition according to any one of Embodiments 1 to 5, wherein the second disintegrator component is one or more selected from crospovidone, croscarmellose sodium, carboxymethyl starch sodium, low substituted hydroxypropylcellulose, and carboxymethylcellulose calcium.

Embodiment 7

The method of producing a disintegrative particulate composition according to any one of Embodiments 1 to 6, wherein the excipient is a sugar or sugar alcohol.

Embodiment 8

The method of producing a disintegrative particulate composition according to any one of Embodiments 1 to 7, wherein the first and second wet granulation steps are carried out by a fluidized-bed granulation process.

Embodiment 9

The method of producing a disintegrative particulate composition according to any one of Embodiments 1 to 8, wherein the first wet granulation step is carried out using the first or second disintegrator component and the excipient.

Embodiment 10

The method of producing a disintegrative particulate composition according to any one of Embodiments 1 to 9, wherein a spray liquid is water or an aqueous solution in which less than 10% of components for the disintegrative particulate composition are dissolved.

Embodiment 11

A disintegrative particulate composition which is obtained by the method for producing a disintegrative particulate composition according to any one of Embodiments 1 to 10.

Embodiment 12

An orally-disintegrating tablet, including the disintegrative particulate composition according to Embodiment 11 and a medicinal ingredient.

Embodiment 13

The orally-disintegrating tablet according to Embodiment 12, having a hardness of 45 to 100 N and a disintegration time in water of 10 to 30 seconds.

Embodiment 14

The orally-disintegrating tablet according to Embodiment 13, having a hardness of 50 to 100 N, a disintegration time in water of 10 to 30 seconds and a disintegration time in the oral cavity of 10 to 30 seconds.

Advantageous Effects of Invention

By blending in an orally-disintegrating tablet, the disintegrative particulate composition of the present invention, including an acid-type carboxymethylcellulose as a disintegrator component, excellent tablet hardness and disintegrability desired for the orally-disintegrating tablet can be imparted to it, and excellent moldability can be provided in production of said tablet.

Furthermore, by blending a crystalline cellulose in the disintegrative particulate composition, more excellent tablet hardness and disintegrability desired for an orally-disintegrating tablet can be imparted to it, and more excellent moldability can be provided in production of said tablet. Such effects are remarkable effects that cannot be predicted from conventional technologies.

DESCRIPTION OF EMBODIMENTS

The present invention relates to (1) a method of producing a disintegrative particulate composition including three components consisting of a first disintegrator component of an acid-type carboxymethylcellulose, a second disintegrator component other than the acid-type carboxymethylcellulose and an excipient, characterized by including: a first wet granulation step using any two of the three components; and a second wet granulation step using at least granules obtained in the first wet granulation step and the remaining one component not used in the first wet granulation step (the first method according to the present invention).

The present invention further relates to a method of producing a disintegrative particulate composition including a crystalline cellulose as a forth component besides the above-described three components. The method can take the following two embodiments:

(2) a method of producing a disintegrative particulate composition, characterized by including a first wet granulation step using any two or three of the four components, and a second wet granulation step using at least granules obtained in the first wet granulation step and the remaining one or two of the four components not used in the first wet granulation step (the second method of the present invention); and (3) a method of producing a disintegrative particulate composition, characterized by including a first wet granulation step using any two of the three components other than the crystalline cellulose, a second wet granulation step using at least granules obtained in the first wet granulation step and the remaining one component not used in the first wet granulation step, and a third step of mixing the crystalline cellulose into granules obtained in the second wet granulation step (the third method of the present invention).

Additionally, each of the above-described four components may be used only in one granulation step. For example, only granules obtained in the first wet granulation step and the remaining component(s) not used in the first wet granulation step can be used in the second wet granulation step. Alternatively, one component can be used in a plurality of granulation steps. For example, each of components such as crystalline cellulose can be used in both the first and second wet granulation steps.

Four mechanisms of "wicking", "swelling", "deformation" and "repulsion" have been proposed as mechanisms of disintegration of tablets or the like. Among them, "wicking" is a disintegration mechanism which proceeds upon weakened binding force between particles included in the tablet as a result of water permeation through components such as disintegrators included in the tablet. As a typical example of a disintegrator having a higher effect to promote such "wicking", an acid-type carboxymethylcellulose has been known. Also, "swelling" is a disintegration mechanism which proceeds upon swelling of disintegrators themselves as a result of water permeation through the disintegrators.

The acid-type carboxymethylcellulose, which is the first disintegrator component included in the disintegrative particulate composition of the present invention, is a substance called carmellose, and has been used as a pharmaceutical additive. In the same manner as the acid-type carboxymethylcellulose, for example, both a calcium salt of carboxymethylcellulose and a cross-linked product of carboxymethylcellulose sodium are water-insoluble, and have been used as disintegrator for tablets, etc. On the other hand, a sodium salt of carboxymethylcellulose is water-soluble, and has been used for purposes of a binder, etc. In addition, in some cases, a salt of carboxymethylcellulose may be referred to as carmellose.

For the second disintegrator component of the disintegrative particulate composition of the present invention, any disintegrators other than the acid-type carboxymethylcellulose which have been known to a person skilled in the art can be used. However, in order to obtain combined effects of the different disintegration mechanisms as shown above, it is preferable that a disintegrator having a superior effect to promote a mechanism other than "wicking" (e.g. "swelling") be used as the second disintegrator component. Suitable examples of such a disintegrator include crospovidone, croscarmellose sodium, carboxymethyl starch sodium, low substituted hydroxypropylcellulose, carboxymethylcellulose calcium, hydroxypropyl starch, and starch. Additionally, crospovidone is a common name for a cross-linked polymer of 1-vinyl-2-pyrrolidone, and croscarmellose sodium is a common name for a cross-linked product of carboxymethylcellulose sodium.

Among them, one, or any combination of two or more selected from crospovidone, croscarmellose sodium, carboxymethyl starch sodium, low substituted hydroxypropylcellulose and carboxymethylcellulose calcium is preferable.

Any compound which has been known to a person skilled in the art as an excipient is included as the third component in the disintegrative particulate composition of the present invention. Typical examples of such a compound include sugars or sugar alcohols such as mannitol, erythritol, sorbitol, D-glucitol (maltitol), xylitol, trehalose, lactose and maltose. Moreover, as preferable examples thereof, mannitol, erythritol, trehalose, sorbitol and D-glucitol (maltitol) can be mentioned. As the excipient, two or more types of compounds properly selected from these compounds can also be used. Furthermore, when excipients are used in each of the first wet granulation step and the second wet granulation step, the excipients may be of the same type (the same combination), or may be of different types (different combinations).

The disintegrative particulate composition produced by the method of the present invention can include a crystalline cellulose known to a person skilled in the art, as the fourth component. As typical examples of such a crystalline cellulose, commercially-available products such as "Avicel" (FMC Corporation), "CEOLUS" (Asahi Kasei Chemicals Corp.), and "VIVAPUR" (RETTENMAIER) can be mentioned.

Furthermore, various types of optional components known to a person skilled in the art may properly be added and mixed into the disintegrative particulate composition of the present invention, for the purpose of adjusting various characteristics such as the disintegrating force, binding force and ease in taking the tablet, without impairing the effects of the present invention according to the above-described three or four components. As examples of such components, fluidizing agents, inorganic excipients, sweetening agents, flavoring agents and coloring agents can be mentioned.

The amount of each component blended in the disintegrative particulate composition of the present invention can properly be determined by a person skilled in the art, depending on, for example, the type of the component, the type and purpose of the medicinal ingredient, which is a target to be used in the disintegrative particulate composition, or the purpose of the final product, i.e. the orally-disintegrating tablet. In general, relative to the total weight of the disintegrative particulate composition, the amount of the first disintegrator component is within a range of 10% to 50% by weight, the amount of the second disintegrator component is within a range of 1% to 20% by weight, the amount of the crystalline cellulose, which is the fourth ingredient, is within a range of 1% to 40% by weight, and the amount of the excipient is within a range of 30% to 89% by weight.

It is preferable that the disintegrative particulate composition of the present invention have the following physical properties:
(1) an average particle size of 50 to 200 microns, e.g. 50 to 150 microns; and
(2) a water content of 0.5% to 6% by weight, e.g. 0.5% to 3% by weight.

In addition, these physical properties are measured by using the following methods and conditions.

The average particle size: 2 g of the disintegrative particulate composition is subjected to a measurement with a φ75 mm automatic shaking sieve device (Type "M-2", Tsutsui Scientific Instruments Co., Ltd.). In addition, "R" in the present specification means a curvature radius.

The water content: 5 g of the disintegrative particulate composition is subjected to a measurement using a halogen water content measuring device (Type "HB43", METTLER TOLEDO K.K.).

In each method of the present invention, the first and second granulation steps are carried out by a method in which each component is dispersed in the presence of water, and the dispersion is dried to form complexes, i.e. by a wet granulation process. As specific examples of a wet granulation process, spray methods such as spray drying, tumbling granulation, agitation granulation and fluidized-bed granulation, the freeze-drying method, kneading granulation, and the like can be mentioned, and the composition can be produced by any of these methods known to a person skilled in the art.

Since disintegrators such as an acid-type carboxymethylcellulose are hydrophilic, by carrying out a manipulation of applying a physical force such as by agitation or the like in the presence of water according to wet granulation, the aggregated state in the dry powder converts into a state in which particles are more dispersed. Dispersion can most easily be carried out by the fluidized-bed granulation process in which dispersion by water spraying and drying are carried out, spray drying, tumbling granulation, agitation granulation, etc., and also, drying speeds in these methods are high. Therefore, these methods are preferable.

Among them, the fluidized-bed granulation process is a granulation method in which water, an aqueous solution including a binder, or the like is sprayed onto powder, while blowing the powder up by hot air, and, for example, adjustment of spraying conditions, etc. is easy in this method. Therefore, the fluidized-bed granulation process is the most preferable method.

A person skilled in the art can properly determine which two types of components among the three components other than the crystalline cellulose are used in the first wet granulation step in the method of the present invention, depending on their types, amounts, etc. For example, the first wet granulation step can be carried out by using either the first or second disintegrator component, and the excipient.

As to specific embodiments of the first method, for example, (1) a method in which two components of a first disintegrator component (or a second disintegrator component) and an excipient are used in the first wet granulation step, and the second disintegrator component (or the first disintegrator component) is used in the second wet granulation step (Examples 1, 3 and 4); (2) a method in which two components of the first and second disintegrator components are used in the first wet granulation step, and an excipient is used in the second wet granulation step (Example 2); and (3) a method in which two components of the first disintegrator component (or the second disintegrator component) and an excipient are used in the first wet granulation step, and two components of the second disintegrator component (or the first disintegrator component) and an excipient are used in the second wet granulation step (Examples 5 to 7) can be mentioned.

Moreover, in the second method of the present invention, a crystalline cellulose is mixed with other component(s) to thereby produce granules in at least either the first wet granulation step or the second wet granulation step. For example, either the first disintegrator component or the second disintegrator component, an excipient and a crystal cellulose can be used to carry out the first wet granulation step, and the remaining disintegrator component can be further added thereto in the second wet granulation step. Alternatively, either the first disintegrator component or the second disintegrator component and an excipient can be used to carry out the first wet granulation step, and a crystal cellulose and the remaining disintegrator component can be further added thereto in the second wet granulation step.

Furthermore, also in the third method of the present invention, a person skilled in the art can properly determine which two types of components among the three components other than the crystalline cellulose are used in the first wet granulation step, depending on their types, amounts, etc. For example, the first wet granulation step can be carried out by using either the first disintegrator component or the second disintegrator component and the excipient.

Various types of optional components, other than the above-described four components, which can be appropriately included in the disintegrative particulate composition of the present invention and which have been known to a person skilled in the art, may be properly added in the first and/or second wet granulation step. Alternatively, these optional components may also be added and mixed in an appropriate granulation step of the third step or subsequent steps.

Furthermore, a person skilled in the art can properly determine various conditions such as the spraying speed, the supply air temperature, the exhaust temperature, and the air supply rate, depending on types or amounts of components, etc.

In both of the first wet granulation step and the second wet granulation step according to the fluidized-bed granulation process, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

Furthermore, the present invention also relates to a disintegrative particulate composition obtained by the above-described production method of the present invention, and an orally-disintegrating tablet including the disintegrative particulate composition and a medicinal ingredient. The orally-disintegrating tablet can include other pharmaceutically-acceptable optional components such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia can be used. In addition, types of the medicinal ingredient and auxiliary agents included therein are not particularly limited. Also, the blending ratios of the disintegrative particulate composition, the medicinal ingredient and optional components are not particularly limited as long as the expected effects of the present invention are brought about, and the blending ratios can properly be determined by a person skilled in the art. The orally-disintegrating tablet can be formulated by any methods known to a person skilled in the art, for example, by tableting.

As already described above, the orally-disintegrating tablet of the present invention has superior tablet hardness and disintegrability. As preferable values, the orally-disintegrating tablet may be characterized by having a hardness of 45 to 100 N, preferably 50 to 150 N, more preferably 70 to 150 (N), still more preferably 80 to 150 N, and by having a disintegration time in water of 10 to 30 seconds, preferably 10 to 24 seconds, more preferably 10 to 20 seconds, and by having a disintegration time in the oral cavity of 10 to 30 seconds, more preferably 10 to 21 seconds.

In addition, contents of all related art documents cited in the present specification are incorporated herein by reference.

Hereinafter, the present invention will more specifically be described with reference to Examples. However, the present invention is not considered to be limited to the Examples.

EXAMPLES

Evaluation on Hardness and Disintegrability Tests

With respect to each of tablets obtained in Examples and Comparative Examples, the hardness, the disintegration time in water and the disintegration time in the oral cavity were measured based on the methods described below. The results of measured hardnesses and disintegration times are shown in Tables 1 to 6.

In addition, values of these physical properties were measured based on the following conditions/methods.

Hardness: a hardness (kgf) was measured with a Kiya hardness tester (Fujiwara Scientific Company Co., Ltd.), and the hardness was calculated in accordance with the following formula.

$$\text{Hardness (N)} = \text{measured hardness (kgf)} \times 9.8$$

Disintegration time in water: a disintegration time in water was measured with a disintegration tester (NT-4HF, TOYAMA SANGYO CO., LTD.) in accordance with the method described in the Japanese Pharmacopoeia (however, an auxiliary disk was not used).

The measurements for the hardness and disintegration time were each repeated six times, and average values thereof were regarded as measurement results.

Disintegration time in the oral cavity: one tablet was taken in the oral cavity, and, while keeping a state in which the tablet was placed between the tongue and the upper jaw without applying any pressure thereto, the time required for the tablet to be completely disintegrated was measured. The measurements were each repeated three times by adults of both sexes, and average values thereof were regarded as measurement results.

The First Method of the Present Invention

Example 1

As the first wet granulation step, 375 g of mannitol (D-mannitol, Merck Ltd.) and 100 g of carmellose (NS-300, GOTOKU CHEMICAL CO., LTD.) were charged to a fluidized-bed granulator (LAB-1, Powrex Corporation), and 240 g of purified water was sprayed onto the resulting mixture at a rate of 24 g/minute to thereby granulate the mixture. Further, as the second wet granulation step, 20 g of crospovidone (Polyplasdone INF-10, ISP Japan) was added to the resulting granules, and 300 g of purified water was sprayed thereto at 8 g/minute to thereby obtain granules (a disintegrative particulate composition of the present invention). 0.5 parts of magnesium stearate (Wako Pure Chemical Industries, Ltd.) was added to 99.5 parts of the obtained granules, and these were mixed. The mixture was then subjected to tableting at a tablet compression force of 6.6 kN with a hydraulic hand press (Osaka Jack Co., Ltd.) to thereby obtain tablets having a diameter of 8.0 mm, R6.5, and a weight of 250 mg. In addition, the granules had the following values for physical properties: (1) an average particle size of 70 microns and (2) a water content of 1.4% by weight.

Example 2

As the first wet granulation step, 100 g of carmellose (NS-300, GOTOKU CHEMICAL CO., LTD.) and 20 g of crospovidone (Polyplasdone INF-10, ISP Japan) were charged to a fluidized-bed granulator (LAB-1, Powrex Corporation), and 240 g of purified water was sprayed onto the resulting mixture at a rate of 12 g/minute to thereby granulate the mixture. Further, as the second wet granulation step, 375 g of mannitol (D-mannitol, Merck Ltd.) was added to the resulting granules, and 300 g of purified water was sprayed thereto at 18 g/minute to thereby obtain granules (a disintegrative particulate composition of the present invention). The obtained granules were used for tableting in the same manner as Example 1, and tablets having a diameter of 8.0 mm, R6.5, and a weight of 250 mg were obtained. In addition, the granules had the following values for physical properties: (1) an average particle size of 98 microns and (2) a water content of 0.94% by weight.

Example 3

As the first wet granulation step, 375 g of mannitol (D-mannitol, Merck Ltd.) and 20 g of crospovidone (Polyplasdone INF-10, ISP Japan) were charged to a fluidized-bed granulator (LAB-1, Powrex Corporation), and 240 g of purified water was sprayed onto the resulting mixture at a rate of 12 g/minute to thereby granulate the mixture. Further, as the second wet granulation step, 100 g of carmellose (NS-300, GOTOKU CHEMICAL CO., LTD.) was added to the resulting granules, and 300 g of purified water was sprayed thereto at 24 g/minute to thereby obtain granules (a disintegrative particulate composition of the present invention). The obtained granules were used for tableting in the same manner as Example 1, and tablets having a diameter of 8.0 mm, R6.5, and a weight of 250 mg were obtained. In addition, the granules had the following values for physical properties: (1) an average particle size of 73 microns and (2) a water content of 1.1% by weight.

Comparative Example 1

375 g of mannitol (D-mannitol, Merck Ltd.), 100 g of carmellose (NS-300, GOTOKU CHEMICAL CO., LTD.) and 20 g of crospovidone (Polyplasdone INF-10, ISP Japan) were charged to a fluidized-bed granulator (LAB-1, Powrex Corporation), and 240 g of purified water was sprayed onto the resulting mixture at a rate of 12 g/minute to thereby obtain granules in one granulation step. The obtained granules were used for tableting in the same manner as Example 1, and tablets having a diameter of 8.0 mm, R6.5, and a weight of 250 mg were obtained.

Comparative Example 2

Granules were obtained in the same conditions as Comparative Example 1 except that 240 g of purified water was sprayed at a rate of 24 g/minute. The obtained granules were used for tableting in the same manner as Example 1, and tablets having a diameter of 8.0 mm, R6.5, and a weight of 250 mg were obtained.

Example 4

Granules were obtained in the same conditions as Example 1 except that 370 g of D-mannitol and 5 g of erythritol were used instead of 375 g of D-mannitol in Example 1. The obtained granules were used for tableting in the same manner as Example 1. Consequently, tablets having a diameter of 8.0 mm, R6.5, and a weight of 250 mg were obtained. In addition, the granules had the following values for physical properties: (1) a particle size of 90 microns and (2) a water content of 1.3% by weight.

Comparative Example A

Granules were obtained in one granulation step in the same conditions as Comparative Example 1 except that 370 g of D-mannitol and 5 g of erythritol were used instead of 375 g of D-mannitol in Comparative Example 1. The obtained granules were used for tableting in the same manner as Example 1. Consequently, tablets having a diameter of 8.0 mm, R6.5, and a weight of 250 mg were obtained.

Example 5

Granules were obtained in the same conditions as Example 1 except that the amount of D-mannitol in the first wet granulation step in Example 1 was changed to 356 g and that 19 g of trehalose and 20 g of crospovidone were used in the second wet granulation step. The obtained granules were used for tableting in the same manner as Example 1. Consequently, tablets having a diameter of 8.0 mm, R6.5, and a weight of 250 mg were obtained. In addition, the granules had the following values for physical properties: (1) a particle size of 141 microns and (2) a water content of 2.1% by weight.

Comparative Example B

Granules were obtained in one granulation step in the same conditions as Comparative Example 1 except that 356 g of D-mannitol and 19 g of trehalose were used instead of 375 g of D-mannitol in Comparative Example 1. The obtained granules were used for tableting in the same manner as Example 1. Consequently, tablets having a diameter of 8.0 mm, R6.5, and a weight of 250 mg were obtained.

Example 6

Tableting was carried out in the same manner as Example 1 except that the amount of D-mannitol in the first wet granulation step in Example 1 was changed to 300 g and that 75 g of maltitol and 20 g of crospovidone were used in the second wet granulation step. Consequently, tablets having a diameter of 8.0 mm, R6.5, and a weight of 250 mg were obtained. In addition, the granules had the following values for physical properties: (1) a particle size of 143 microns and (2) a water content of 1.6%.

Comparative Example C

Granules were obtained in one granulation step in the same conditions as Comparative Example 1 except that 300 g of D-mannitol and 75 g of maltitol were used instead of 375 g of D-mannitol in Comparative Example 1. The obtained granules were used for tableting in the same manner as Example 1. Consequently, tablets having a diameter of 8.0 mm, R6.5, and a weight of 250 mg were obtained.

Example 7

Granules were obtained in the same conditions as Example 1 except that the amount of D-mannitol in the first wet granulation step in Example 1 was changed to 356 g and that 19 g of sorbitol and 20 g of crospovidone were used in the second wet granulation step. The obtained granules were used for tableting in the same manner as Example 1. Consequently, tablets having a diameter of 8.0 mm, R6.5, and a weight of 250 mg were obtained. In addition, the granules had the following values for physical properties: (1) a particle size of 188 microns and (2) a water content of 1.9%.

Comparative Example D

Granules were obtained in one granulation step in the same conditions as Comparative Example 1 except that 356 g of D-mannitol and 19 g of sorbitol were used instead of 375 g of D-mannitol in Comparative Example 1. The obtained granules were used for tableting in the same manner as Example 1. Consequently, tablets having a diameter of 8.0 mm, R6.5, and a weight of 250 mg were obtained.

TABLE 1

| Production methods for disintegrative particulate composition | Example 1 | Example 2 | Example 3 | Comparative Example 1 | Comparative Example 2 |
|---|---|---|---|---|---|
| Tablet compression force (KN) | 6.6 | 6.6 | 6.6 | 6.6 | 6.6 |
| Hardness (N) | 58 | 50 | 52 | 34 | 40 |
| Disintegrative time in water (seconds) | 15 | 13 | 13 | 21 | 17 |

In addition, each of the disintegrative particulate compositions obtained by the methods of Examples 1, 2 and 3 was subjected to tableting in the same method described in each of the Examples except that the tablet compression force was changed to 8.3 KN. In that case, results obtained by subjecting the obtained tablets to the measurements of the hardness and disintegration times in water in the same manner as the cases in Table 1 are shown in Table 2.

TABLE 2

| Production methods for disintegrative particulate composition | Example 1 | Example 2 | Example 3 |
|---|---|---|---|
| Tablet compression force (KN) | 8.3 | 8.3 | 8.3 |
| Hardness (N) | 84 | 68 | 72 |
| Disintegrative time in water (seconds) | 17 | 12 | 16 |

Furthermore, each of the disintegrative particulate compositions obtained by the methods of Examples 3 to 7 and corresponding Comparative Examples A to D was subjected to tableting in the same method described in each of the Examples except that the tablet compression force was changed to 8.3 KN. In that case, results obtained by subjecting the obtained tablets to the measurements of the hardness and disintegration times in water in the same manner as the cases in Table 1 are shown in Table 3.

TABLE 3

| Excipients: mannitol and erythritol | | Tablet compression forces | |
|---|---|---|---|
| | | 6.6 kN | 8.3 kN |
| Two-stage granulation (Example 4) | Hardness (N) | 49 | 68 |
| | Disintegration time in water (s) | 15 | 17 |
| One-stage granulation (Comparative Example A) | Hardness (N) | 30 | 46 |
| | Disintegration time in water (s) | 12 | 15 |

| Excipients: mannitol and trehalose | | Tablet compression force 6.6 kN |
|---|---|---|
| Two-stage granulation (Example 5) | Hardness (N) | 64 |
| | Disintegration time in water (s) | 23 |
| One-stage granulation (Comparative Example B) | Hardness (N) | 44 |
| | Disintegration time in water (s) | 18 |

TABLE 3-continued

| Excipients: mannitol and maltitol | | Tablet compression forces | |
|---|---|---|---|
| | | 6.0 kN | 8.0 kN |
| Two-stage granulation (Example 6) | Hardness (N) | 50 | 63 |
| | Disintegration time in water (s) | 24 | 28 |
| One-stage granulation (Comparative Example C) | Hardness (N) | 63 | 73 |
| | Disintegration time in water (s) | 115 | >200 |

| Excipients: mannitol and sorbitol | | 6.0 kN | 8.0 kN |
|---|---|---|---|
| Two-stage granulation (Example 7) | Hardness (N) | 46 | 56 |
| | Disintegration time in water (s) | 19 | 23 |
| One-stage granulation (Comparative Example D) | Hardness (N) | 28 | 37 |
| | Disintegration time in water (s) | 16 | 18 |

Based on the results shown in Tables 1 to 3, it was proven that, regardless of which two types of components among the first disintegrator component, the second disintegrator component and the excipient were used in the first wet granulation step, the tablets obtained by using granules (disintegrative particulate compositions of the present invention) produced by the methods of the present invention including the first wet granulation step and the second wet granulation step in Examples 1 to 7 had superior tablet hardness and disintegrability as well as superior moldability through which higher tablet hardness was obtained by smaller tablet compression forces, as compared with tablets obtained by using granules which were produced by conventional methods of granulating the components together in one step.

The Second Method of the Present Invention

Example 8

Production of a Disintegrative Particulate Composition

As the first wet granulation step, 280 g of mannitol (D-mannitol, Merck Ltd.), 75 g of carmellose (NS-300, GOTOKU CHEMICAL CO., LTD.) and 100 g of a crystalline cellulose (CEOLUS PH-101, Asahi Kasei Chemicals Corp.) were charged to a fluidized-bed granulator (LAB-1, Powrex Corporation), and 240 g of purified water was sprayed onto the resulting mixture at a rate of 24 g/minute to thereby granulate the mixture. Further, as the second wet granulation step, 40 g of crospovidone (Polyplasdone INF-10, ISP Japan) was added to the resulting granules, and 300 g of purified water was sprayed thereto at 10 g/minute to thereby obtain granules (a disintegrative particulate composition of the present invention). 0.5 parts by weight of magnesium stearate (Taihei Chemical Industrial Co. Ltd.) was added to 99.5 parts by weight of the obtained granules, and these were mixed. The mixture was then subjected to tableting at tablet compression forces of 6.0 kN and 8.0 kN with a simple tableting machine (ICHIHASHI-SEIKI Co., Ltd.) to thereby obtain tablets having a diameter of 8.0 mm, R6.5, and a weight of 250 mg. In addition, the granules had the following values for physical properties: (1) an average particle size of 93 microns and (2) a water content of 2.3% by weight.

Example 9

Production of a Disintegrative Particulate Composition

As the first wet granulation step, 280 g of mannitol (D-mannitol, Merck Ltd.) and 75 g of carmellose (NS-300, GOTOKU CHEMICAL CO., LTD.) were charged to a fluidized-bed granulator (LAB-1, Powrex Corporation), and 227 g of purified water was sprayed onto the resulting mixture at a rate of 24 g/minute to thereby granulate the mixture. Further, as the second wet granulation step, 40 g of crospovidone (Polyplasdone INF-10, ISP Japan) and 100 g of a crystalline cellulose (CEOLUS PH-101, Asahi Kasei Chemicals Corp.) were added to the resulting granules, and 300 g of purified water was sprayed thereto at 10 g/minute to thereby obtain granules (a disintegrative particulate composition of the present invention). The obtained granules were used for tableting in the same manner as Example 8 to thereby obtain tablets having a diameter of 8.0 mm, R6.5, and a weight of 250 mg. In addition, the granules had the following values for physical properties: (1) an average particle size of 93 microns and (2) a water content of 1.8% by weight.

Example 10

Production of a Disintegrative Particulate Composition

Granulation was carried out in the same conditions as Example 8 except that the amount of D-mannitol and the amount of the crystalline cellulose in the first wet granulation step of Example 8 were changed to 255 g and 125 g, respectively, to thereby obtain granules (a disintegrative particulate composition of the present invention). The obtained granules were used for tableting in the same manner as Example 8. Consequently, tablets having a diameter of 8.0 mm, R6.5, and a weight of 250 mg were obtained. In addition, the granules had the following values for physical properties: (1) an average particle size of 87 microns and (2) a water content of 2.2% by weight.

Example 11

Production of a Disintegrative Particulate Composition

Granulation was carried out in the same conditions as Example 8 except that the amount of D-mannitol in the first wet granulation step in Example 8 was changed to 270 g and that the amount of crospovidone was changed to 50 g in the second wet granulation step, to thereby obtain granules (a disintegrative particulate composition of the present invention). The obtained granules were used for tableting in the same manner as Example 8. Consequently, tablets having a diameter of 8.0 mm, R6.5, and a weight of 250 mg were obtained. In addition, the granules had the following values for physical properties: (1) an average particle size of 100 microns and (2) a water content of 2.1% by weight.

Example 12

Production of a Disintegrative Particulate Composition

As the first wet granulation step, 280 g of mannitol (D-mannitol, Merck Ltd.) and 40 g of crospovidone (Polyplasdone INF-10, ISP Japan) were charged to a fluidized-bed granulator (LAB-1, Powrex Corporation), and 179 g of purified water was sprayed onto the resulting mixture at a rate of 12 g/minute to thereby granulate the mixture. Further, as the second wet granulation step, 75 g of carmellose (NS-300, GOTOKU CHEMICAL CO., LTD.) and 100 g of a crystalline cellulose (CEOLUS PH-101, Asahi Kasei Chemicals Corp.) were added to the resulting granules, and 300 g of purified water was sprayed thereto at 12 g/minute to thereby obtain granules (a disintegrative particulate composition of the present invention). The obtained granules were used for tableting in the same manner as Example 8 to thereby obtain tablets having a diameter of 8.0 mm, R6.5, and a weight of 250 mg. In addition, the granules had the following values for physical properties: (1) an average particle size of 81 microns and (2) a water content of 2.5% by weight.

Example 13

Production of a Disintegrative Particulate Composition

As the first wet granulation step, 140 g of mannitol (D-mannitol, Merck Ltd.), 100 g of a crystalline cellulose (CEOLUS PH-101, Asahi Kasei Chemicals Corp.) and 40 g of crospovidone (Polyplasdone INF-10, ISP Japan) were charged to a fluidized-bed granulator (LAB-1, Powrex Corporation), and 155 g of purified water was sprayed onto the resulting mixture at a rate of 12 g/minute to thereby granulate the mixture. Further, as the second wet granulation step, 140 g of mannitol (D-mannitol, Merck Ltd.) and 75 g of carmellose (NS-300, GOTOKU CHEMICAL CO., LTD.) were added to the resulting granules, and 300 g of purified water was sprayed thereto at 12 g/minute to thereby obtain granules (a disintegrative particulate composition of the present invention). 0.5 parts by weight of magnesium stearate (Taihei Chemical Industrial Co. Ltd.) was added to 99.5 parts by weight of the obtained granules, and these were mixed. The mixture was then subjected to tableting at tablet compression forces of 6.0 kN and 8.0 kN with a simple tableting machine (HANDTAB-100, ICHIHASHI-SEIKI Co., Ltd.) to thereby obtain tablets having a diameter of 8.0 mm, R6.5, and a weight of 250 mg. In addition, the granules had the following values for physical properties: (1) an average particle size of 90 microns and (2) a water content of 2.5% by weight.

Comparative Example 3

280 g of mannitol (D-mannitol, Merck Ltd.), 75 g of carmellose (NS-300, GOTOKU CHEMICAL CO., LTD.), 100 g of a crystalline cellulose (CEOLUS PH-101, Asahi Kasei Chemicals Corp.) and 40 g of crospovidone (Polyplasdone INF-10, ISP Japan) were charged to a fluidized-bed granulator (LAB-1, Powrex Corporation), and 300 g of purified water was sprayed onto the resulting mixture at a rate of 12 g/minute to thereby obtain granules in one granulation step. The obtained granules were used for tableting in the same manner as Example 8, and, consequently, tablets having a diameter of 8.0 mm, R6.5, and a weight of 250 mg were obtained.

TABLE 4

| Tablets | Example 8 | | Example 9 | | Example 10 | | Example 11 | |
|---|---|---|---|---|---|---|---|---|
| Tablet compression force (kN) | 6.0 | 8.0 | 6.0 | 8.0 | 6.0 | 8.0 | | |
| Hardness (N) | 90 | 116 | 83 | 108 | 104 | 91 | | |
| Disintegration time in water (seconds) | 16 | 24 | 13 | 17 | 15 | 15 | | |

| Tablets | Comparative Example 3 | |
|---|---|---|
| Tablet compression force (kN) | 6.0 | 8.0 |
| Hardness (N) | 59 | 81 |
| Disintegration time in water (seconds) | 12 | 13 |

The disintegration times in water of tablets obtained in Examples 8 to 13 and Comparative Example 3 were below 30 seconds, and it was proved that Examples 8 to 13 substantially maintained sufficient disintegrability regardless of their higher tablet hardness, compared with Comparative Example 3.

The Third Method of the Present Invention

Example 14

Production of an Orally-Disintegrating Tablet

As the first wet granulation step, 75 g of carmellose (NS-300, GOTOKU CHEMICAL CO., LTD.) and 40 g of crospovidone (Polyplasdone INF-10, ISP Japan) were charged to a fluidized-bed granulator (LAB-1, Powrex Corporation), and 240 g of purified water was sprayed onto the resulting mixture at a rate of 12 g/minute to thereby granulate the mixture. Further, as the second wet granulation step, 380 g of mannitol (D-mannitol, Merck Ltd.) was added to the resulting granules, and 300 g of purified water was sprayed thereto at 18 g/minute to thereby obtain granules (I). In addition, the granules (I) had the following values for physical properties: (1) an average particle size of 108 microns and (2) a water content of 0.9% by weight. As the third step, 49.5 parts by weight of the granules (I) obtained in this way, and 20 parts by weight of a crystalline cellulose (CEOLUS PH-101, Asahi Kasei Chemicals Corp.) were mixed to thereby obtain a disintegrative particulate composition of the present invention. In addition, this disintegrative particulate composition had the following values for physical properties: (1) an average particle size of 98 microns and (2) a water content of 2.0% by weight. Further, 30 parts by weight of N-(4-hydroxyphenyl)acetamide (Acetaminophen), and 0.5 parts by weight of magnesium stearate (Taihei Chemical Industrial Co. Ltd.) were added to 69.5 parts by weight of the disintegrative particulate composition, and these were mixed. The mixture was then subjected to tableting at tablet compression forces of 6.6 kN and 8.3 kN with a hydraulic hand press (Osaka Jack Co., Ltd.) to thereby obtain tablets having a diameter of 8.0 mm, R6.5, and a weight of 250 mg.

Example 15

Production of an Orally-Disintegrating Tablet

As a third step, 39.5 parts by weight of the granules (I) obtained in Example 14 and 30 parts by weight of a crystalline cellulose (CEOLUS PH-101, Asahi Kasei Chemicals Corp.) were mixed to obtain a disintegrative particulate composition of the present invention. In addition, this disintegrative particulate composition had the following values for physical properties: (1) an average particle size of 88 microns and (2) a water content of 2.3% by weight. 30 parts by weight of acetaminophen, and 0.5 parts by weight of magnesium stearate (Taihei Chemical Industrial Co. Ltd.) were added to 69.5 parts by weight of the disintegrative particulate composition, and these were mixed. The mixture was then subjected to tableting at tablet compression forces of 6.6 kN and 8.3 kN with a hydraulic hand press (Osaka Jack Co., Ltd.) to thereby obtain tablets having a diameter of 8.0 mm, R6.5, and a weight of 250 mg.

Example 16

Production of an Orally-Disintegrating Tablet

As a third step, 69.5 parts by weight of the granules (I) obtained in Example 14 and 30 parts by weight of a crystalline cellulose (CEOLUS PH-101, Asahi Kasei Chemicals Corp.) were mixed to obtain a disintegrative particulate composition of the present invention. In addition, this disintegrative particulate composition had the following values for physical properties: (1) an average particle size of 102 microns and (2) a water content of 1.8% by weight. 0.5 parts by weight of magnesium stearate (Taihei Chemical Industrial Co. Ltd.) was added to the disintegrative particulate composition, and these were mixed. The mixture was then subjected to tableting at tablet compression forces of 6.6 kN and 8.3 kN with a hydraulic hand press (Osaka Jack Co., Ltd.) to thereby obtain tablets having a diameter of 8.0 mm, R6.5, and a weight of 250 mg.

Example 17

Production of an Orally-Disintegrating Tablet

Granulation was carried out in the same conditions as Example 14 except that 40 g of carboxymethylcellulose calcium (ECG-505, GOTOKU CHEMICAL CO., LTD.) was used instead of 40 g of crospovidone in the first wet granulation step in Example 14, thereby obtaining granules (II). In addition, the granules (II) had the following values for physical properties: (1) an average particle size of 89 microns and (2) a water content of 1.1%. As a third step, 79.5 parts by weight of the obtained granules (II) and 20 parts by weight of a crystalline cellulose (CEOLUS PH-101, Asahi Kasei Chemicals Corp.) were mixed to thereby obtain a disintegrative particulate composition of the present invention. In addition, this disintegrative particulate composition had the following values for physical properties: (1) an average particle size of 102 microns and (2) a water content of 2.0% by weight. Further, 0.5 parts by weight of magnesium stearate (Taihei Chemical Industrial Co. Ltd.) was added to the disintegrative particulate composition, and these were mixed. The mixture was then subjected to tableting at tablet compression forces of 6.0 kN and 8.0 kN with a simple tableting machine (HANDTAB-100, ICHIHASHI-SEIKI Co., Ltd.) to thereby obtain tablets having a diameter of 8.0 mm, R6.5, and a weight of 250 mg.

Example 18

Production of an Orally-Disintegrating Tablet

Granulation was carried out in the same conditions as Example 14 except that 40 g of croscarmellose sodium (ND-2HS, Asahi Kasei Chemicals Corp.) was used instead of 40 g of crospovidone in the first wet granulation step in Example 14, thereby obtaining granules (III). In addition, the granules (III) had the following values for physical properties: (1) an average particle size of 89 microns and (2) a water content of 1.0%. As a third step, 79.5 parts by weight of the obtained granules (III) and 20 parts by weight of a crystalline cellulose (CEOLUS PH-101, Asahi Kasei Chemicals Corp.) were mixed to thereby obtain a disintegrative particulate composition of the present invention. In addition, this disintegrative particulate composition had the following values for physical properties: (1) an average particle size of 95 microns and (2) a water content of 2.1% by weight. Further, 0.5 parts by weight of magnesium stearate (Taihei Chemical Industrial Co. Ltd.) was added to the disintegrative particulate composition, and these were mixed. The mixture was then subjected to tableting at tablet compression forces of 6.0 kN and 8.0 kN with a simple tableting machine (HANDTAB-100, ICHIHASHI-SEIKI Co., Ltd.) to thereby obtain tablets having a diameter of 8.0 mm, R6.5, and a weight of 250 mg.

Comparative Example 4

99.5 parts by weight of the granules (I) obtained in Example 14 and 0.5 parts by weight of magnesium stearate (Taihei Chemical Industrial Co. Ltd.) were mixed, and tablets were obtained in the same manner as Example 1.

Comparative Example 5

99.5 parts by weight of the granules (II) obtained in Example 17 and 0.5 parts by weight of magnesium stearate (Taihei Chemical Industrial Co. Ltd.) were mixed, and tablets were obtained in the same manner as Example 1.

Comparative Example 6

99.5 parts by weight of the granules (III) obtained in Example 18 and 0.5 parts by weight of magnesium stearate (Taihei Chemical Industrial Co. Ltd.) were mixed, and tablets were obtained in the same manner as Example 1.

TABLE 5

| | Unit (parts by weight) | | | |
|---|---|---|---|---|
| | Granule (I) | Crystalline cellulose | Acetaminophen | Magnesium stearate |
| Example 14 | 49.5 | 20 | 30 | 0.5 |
| Example 15 | 39.5 | 30 | 30 | 0.5 |
| Example 16 | 69.5 | 30 | 0 | 0.5 |
| Example 17 | 79.5 | 20 | 0 | 0.5 |
| Example 18 | 79.5 | 20 | 0 | 0.5 |
| Comparative Example 4 | 99.5 | 0 | 0 | 0.5 |
| Comparative Example 5 | 99.5 | 0 | 0 | 0.5 |
| Comparative Example 6 | 99.5 | 0 | 0 | 0.5 |

TABLE 6

| Tablets | Example 14 | | Example 15 | | Example 16 | |
|---|---|---|---|---|---|---|
| Tablet compression force (kN) | 6.6 | 8.3 | 6.6 | 8.3 | 6.6 | 8.3 |
| Hardness (N) | 21 | 35 | 35 | 47 | 73 | 97 |
| Disintegration time in water (seconds) | 11 | 12 | 11 | 12 | 13 | 17 |

TABLE 6-continued

| Tablets | Example 17 | Example 18 | Comparative Example 4 | | Comparative Example 5 | Comparative Example 6 |
|---|---|---|---|---|---|---|
| Tablet compression force (kN) | 8.0 | 8.0 | 6.6 | 8.3 | 8.3 | 8.3 |
| Hardness (N) | 45 | 48 | 50 | 68 | 37 | 39 |
| Disintegration time in water (seconds) | 11 | 12 | 13 | 12 | 15 | 16 |

When comparing Examples 16 to 18 with Comparative Examples 4 to 6, respectively, based on the results shown in Table 6, it was proven that orally-disintegrating tables having higher tablet hardness while maintaining sufficient disintegrability could be produced by using disintegrative particulate compositions which were obtained by further mixing a crystalline cellulose, as a third step, into granules (I) to (III) produced by the methods of the present invention including two-stage wet granulation steps including the first and second wet granulation steps, as compared with the Comparative Examples.

INDUSTRIAL APPLICABILITY

The present invention significantly contributes to research and development of orally-disintegrating tablets having excellent tablet hardness and disintegrability.

What is claimed is:

1. A method of producing an orally-disintegrating particulate composition which comprises: three components consisting of a first disintegrator component of acid-type carboxymethylcellulose, a second disintegrator component other than the acid-type carboxymethylcellulose and an excipient, the method comprising:
    a first wet granulation step adding any two of the three components;
    a second wet granulation step adding at least granules obtained in the first wet granulation step and the remaining component not added in the first wet granulation step to produce the orally-disintegrating particulate composition; and
    tableting the orally-disintegrating particulate composition, thereby forming an orally-disintegrating tablet having
    (i) a hardness from 58 to 150 N, or
    (ii) a hardness from 52 to 150 N and a disintegration time in water from 10 to 24 seconds,
    wherein the second disintegrator component is one or more selected from crospovidone, croscarmellose sodium, carboxymethyl starch sodium, and carboxymethylcellulose calcium.

2. The method of producing an orally-disintegrating particulate composition according to claim 1, wherein the orally-disintegrating particulate composition further comprises a crystalline cellulose as a fourth component, and the method comprises a first wet granulation step adding any two or three of the four components and a second wet granulation step adding at least the granules obtained in the first wet granulation step and the remaining one or two of the four components not added in the first wet granulation step.

3. The method of producing an orally-disintegrating particulate composition according to claim 1, wherein the orally-disintegrating particulate composition further comprises a crystalline cellulose as a fourth component, and the method comprises a first wet granulation step adding any two of the three components other than the crystalline cellulose, a second wet granulation step adding at least the granules obtained in the first wet granulation step and the remaining one component not added in the first wet granulation step, and a third step of mixing the crystalline cellulose into granules obtained in the second wet granulation step.

4. The method of producing an orally-disintegrating particulate composition according to claim 1, wherein each of the three components is added only in one of the first and second wet granulation steps.

5. The method of producing an orally-disintegrating particulate composition according to claim 4, wherein the second wet granulation step adds the remaining one component not added in the first wet granulation step to the granules obtained in the first wet granulation step.

6. The method of producing an orally-disintegrating particulate composition according to claim 1, wherein the excipient is a sugar or sugar alcohol.

7. The method of producing an orally-disintegrating particulate composition according to claim 1, wherein the first and second wet granulation steps are carried out by a fluidized-bed granulation process.

8. The method of producing an orally-disintegrating particulate composition according to claim 1, wherein the first wet granulation step comprises adding (1) the first disintegrator component and the excipient, or (2) the second disintegrator component and the excipient.

9. The method of producing an orally-disintegrating particulate composition according to claim 1, wherein a spray liquid is (1) water, or (2) an aqueous solution in which less than 10% of components for the orally-disintegrating particulate composition are dissolved.

10. The method of producing an orally-disintegrating particulate composition according to claim 1, wherein the first wet granulation step comprises spraying the any two of the three components with a liquid.

11. The method of producing an orally-disintegrating particulate composition according to claim 10, wherein the liquid comprises water.

12. The method of producing an orally-disintegrating particulate composition according to claim 1, wherein the second wet granulation step comprises spraying the at least granules obtained in the first step and the remaining component not added in the first granulation step with a liquid.

13. The method of producing an orally-disintegrating particulate composition according to claim 12, wherein the liquid comprises water.

14. The method of producing an orally-disintegrating particulate composition according to claim 1, wherein the orally-disintegrating tablet has a hardness from 52 to 150 N and a disintegration time in water from 10 to 24 seconds.

15. The method of producing an orally-disintegrating particulate composition according to claim 1, wherein the orally-disintegrating tablet has a hardness from 70 to 150 N.

16. The method of producing an orally-disintegrating particulate composition according to claim 1, wherein the orally-disintegrating tablet has a disintegration time in water from 10 to 19 seconds.

17. The method of producing an orally-disintegrating particulate composition according to claim 1, wherein the orally-disintegrating tablet has a disintegration time in water from 10 to 16 seconds.

18. The method of producing an orally-disintegrating particulate composition according to claim 1, wherein the orally-disintegrating particulate composition comprises from 10 to 50% by weight of the first disintegrator component, from 1 to 20% by weight of the second disintegrator component, and from 30 to 89% by weight of the excipient.

19. The method of producing an orally-disintegrating particulate composition according to claim 1, wherein the orally-disintegrating tablet has a hardness from 58 to 150 N.

20. The method of producing an orally-disintegrating particulate composition according to claim 1, wherein the orally-disintegrating tablet has a hardness from 64 to 150 N.

* * * * *